(12) United States Patent
Scofield et al.

(10) Patent No.: US 10,629,075 B2
(45) Date of Patent: Apr. 21, 2020

(54) PROVIDING USERS WITH ACCESS TO ROUTES FOR TRAVELING

(71) Applicant: INRIX INC., Kirkland, WA (US)

(72) Inventors: Christopher L. Scofield, Seattle, WA (US); Dominic Jordan, Manchester (GB); Uri Lavee, Tel Aviv (IL); Kevin James Foreman, Sammamish, WA (US); William Schwebel, Seattle, WA (US)

(73) Assignee: INRIX, Inc., Kirkland, WA (US)

( * ) Notice: Subject to any disclaimer, the term of this patent is extended or adjusted under 35 U.S.C. 154(b) by 426 days.

(21) Appl. No.: 15/122,677

(22) PCT Filed: Mar. 2, 2015

(86) PCT No.: PCT/US2015/018364
§ 371 (c)(1),
(2) Date: Aug. 31, 2016

(87) PCT Pub. No.: WO2015/134410
PCT Pub. Date: Sep. 11, 2015

(65) Prior Publication Data
US 2017/0069001 A1   Mar. 9, 2017

Related U.S. Application Data

(60) Provisional application No. 61/946,962, filed on Mar. 3, 2014.

(51) Int. Cl.
*G08G 1/0967*      (2006.01)
*G08G 1/0968*      (2006.01)
(Continued)

(52) U.S. Cl.
CPC ... *G08G 1/096791* (2013.01); *A61B 5/02055* (2013.01); *A61B 5/0476* (2013.01);
(Continued)

(58) Field of Classification Search
CPC ....... G08G 1/096791; G08G 1/096822; G08G 1/0967; G08G 1/07; G07B 15/00; G06Q 2240/00
See application file for complete search history.

(56) References Cited

U.S. PATENT DOCUMENTS 6,317,721 B1 * 11/2001 Hurta .................. G06Q 20/363
                                                    235/384
8,285,731 B2 * 10/2012 Peeters ................ G08G 1/0104
                                                    707/754

(Continued)

OTHER PUBLICATIONS

"A Shoulder to Drive on", May 5 2012, https://web.archive.org/web/20120505232522/https:/www.traffictechnologytoday.com/opinion.php?BlogID=109 (Year: 2012).*

(Continued)

*Primary Examiner* — Rupangini Singh
*Assistant Examiner* — Ismail A Manejwala
(74) *Attorney, Agent, or Firm* — Cooper Legal Group, LLC

(57) ABSTRACT

Among other things, one or more techniques and/or systems are provided for providing users with access to a route for travelling. A user, of a client device, may send a request for access to the route to a route planning service. The route may correspond to a starting location and an ending location. The route planning service may query a route database to identify an entry indicating that a restricted access road segment (e.g., a high occupancy vehicle lane, a shoulder lane, a bus lane, etc.) and/or a road segment (e.g., comprising a traffic light alteration capability) exists between the starting location and the ending location. Responsive to successfully authorizing the user for travelling the restricted access road segment and/or the road segment, the route, comprising the restricted access road segment and/or the road segment, may be provided to the client device.

20 Claims, 11 Drawing Sheets

(51) Int. Cl.

| | | |
|---|---|---|
| G08G 1/07 | (2006.01) | |
| G07B 15/00 | (2011.01) | |
| H04W 4/50 | (2018.01) | |
| G06N 20/00 | (2019.01) | |
| G06F 16/29 | (2019.01) | |
| H04W 4/024 | (2018.01) | |
| H04W 4/029 | (2018.01) | |
| G08G 1/01 | (2006.01) | |
| B60W 40/08 | (2012.01) | |
| B60W 40/09 | (2012.01) | |
| G08G 1/09 | (2006.01) | |
| G07B 15/06 | (2011.01) | |
| G08G 1/097 | (2006.01) | |
| B60W 30/14 | (2006.01) | |
| G05D 1/00 | (2006.01) | |
| G07C 5/00 | (2006.01) | |
| A61B 5/0205 | (2006.01) | |
| A61B 5/0476 | (2006.01) | |
| A61B 5/00 | (2006.01) | |
| G05D 1/02 | (2020.01) | |
| H04B 1/3822 | (2015.01) | |
| H04L 29/08 | (2006.01) | |
| B64C 39/02 | (2006.01) | |
| H04B 7/185 | (2006.01) | |
| G06Q 20/10 | (2012.01) | |
| G06Q 30/02 | (2012.01) | |
| H04W 12/08 | (2009.01) | |
| H04M 15/00 | (2006.01) | |
| G06Q 40/08 | (2012.01) | |
| H04L 9/32 | (2006.01) | |
| B60R 16/023 | (2006.01) | |
| G08G 1/065 | (2006.01) | |
| G01C 21/36 | (2006.01) | |
| H04W 4/42 | (2018.01) | |
| H04W 4/40 | (2018.01) | |
| G01C 21/34 | (2006.01) | |
| G08G 1/0962 | (2006.01) | |
| G08G 1/0965 | (2006.01) | |
| H04W 4/48 | (2018.01) | |
| A61B 5/024 | (2006.01) | |
| A61B 5/053 | (2006.01) | |
| G06Q 50/30 | (2012.01) | |

(52) U.S. Cl.
CPC ........ *A61B 5/4845* (2013.01); *B60R 16/0236* (2013.01); *B60W 30/143* (2013.01); *B60W 40/08* (2013.01); *B60W 40/09* (2013.01); *B64C 39/024* (2013.01); *G01C 21/3415* (2013.01); *G01C 21/3469* (2013.01); *G01C 21/3617* (2013.01); *G01C 21/3655* (2013.01); *G01C 21/3667* (2013.01); *G01C 21/3682* (2013.01); *G05D 1/0011* (2013.01); *G05D 1/0088* (2013.01); *G05D 1/021* (2013.01); *G06F 16/29* (2019.01); *G06N 20/00* (2019.01); *G06Q 20/102* (2013.01); *G06Q 30/0283* (2013.01); *G06Q 40/08* (2013.01); *G07B 15/00* (2013.01); *G07B 15/063* (2013.01); *G07C 5/008* (2013.01); *G08G 1/012* (2013.01); *G08G 1/0112* (2013.01); *G08G 1/0129* (2013.01); *G08G 1/0141* (2013.01); *G08G 1/0145* (2013.01); *G08G 1/065* (2013.01); *G08G 1/07* (2013.01); *G08G 1/093* (2013.01); *G08G 1/097* (2013.01); *G08G 1/0962* (2013.01); *G08G 1/0965* (2013.01); *G08G 1/0967* (2013.01); *G08G 1/096725* (2013.01); *G08G 1/096741* (2013.01); *G08G 1/096775* (2013.01); *G08G 1/096811* (2013.01); *G08G 1/096822* (2013.01); *G08G 1/096838* (2013.01); *H04B 1/3822* (2013.01); *H04B 7/18504* (2013.01); *H04L 9/3247* (2013.01); *H04L 67/02* (2013.01); *H04L 67/306* (2013.01); *H04M 15/60* (2013.01); *H04W 4/024* (2018.02); *H04W 4/029* (2018.02); *H04W 4/40* (2018.02); *H04W 4/42* (2018.02); *H04W 4/50* (2018.02); *H04W 12/08* (2013.01); *A61B 5/024* (2013.01); *A61B 5/0531* (2013.01); *B60W 2040/0809* (2013.01); *B60W 2040/0872* (2013.01); *B60W 2540/22* (2013.01); *B60W 2550/12* (2013.01); *B60W 2550/14* (2013.01); *B60W 2710/1044* (2013.01); *B60W 2710/18* (2013.01); *B60W 2720/10* (2013.01); *B64C 2201/123* (2013.01); *G01C 21/3608* (2013.01); *G06Q 50/30* (2013.01); *G06Q 2240/00* (2013.01); *H04W 4/48* (2018.02)

(56) References Cited

U.S. PATENT DOCUMENTS

| | | | | |
|---|---|---|---|---|
| 8,370,053 | B2* | 2/2013 | Li | G08G 1/01 340/995.1 |
| 9,230,435 | B2* | 1/2016 | Taylor | G08G 1/087 |
| 2001/0037174 | A1 | 11/2001 | Dickerson | |
| 2005/0021365 | A1* | 1/2005 | Nakfoor | G06F 21/33 235/382 |
| 2006/0015394 | A1* | 1/2006 | Sorensen | G06Q 40/00 705/13 |
| 2006/0080029 | A1 | 4/2006 | Kodani et al. | |
| 2006/0250250 | A1 | 11/2006 | Youn | |
| 2008/0300776 | A1 | 12/2008 | Petrisor et al. | |
| 2009/0024309 | A1 | 1/2009 | Crucs | |
| 2010/0057358 | A1 | 3/2010 | Winer et al. | |
| 2010/0082226 | A1* | 4/2010 | Mukherjee | G08G 1/0104 701/118 |
| 2012/0215594 | A1* | 8/2012 | Gravelle | G07B 15/02 705/13 |
| 2013/0073112 | A1* | 3/2013 | Phelan | G06Q 40/00 701/1 |
| 2013/0024309 | A1 | 8/2013 | Zou et al. | |
| 2014/0118168 | A1* | 5/2014 | Lee | G08G 1/096725 340/905 |
| 2014/0172521 | A1* | 6/2014 | Itaya | G07B 15/06 705/13 |
| 2015/0199664 | A1* | 7/2015 | Buckman | G06Q 20/145 705/13 |
| 2016/0209219 | A1* | 7/2016 | Grush | H04W 4/029 |
| 2017/0358025 | A1* | 12/2017 | Varma | G06Q 30/08 |

OTHER PUBLICATIONS

IBM, Algorithm and Device to Optimize Approach to Traffic Control Signals, Mar. 11, 2009, IP.com (Year: 2009).*
EP Search Report cited in EP Application No. 15757727.1 dated Nov. 7, 2017, 8 pgs.
Corresponding International Application No. PCT/US2015/018364, International Search report and written opinion dated Jun. 16, 2015.

* cited by examiner

PROVIDING USERS WITH ACCESS TO ROUTES FOR TRAVELING

CROSS-REFERENCE TO RELATED APPLICATIONS

This application claims priority to U.S. Provisional Patent Application No. 61/946,962 titled "DETERMINING HOV/HOT LANE TRAVEL TIMES", filed on Mar. 3, 2014, which is hereby incorporated by reference.

BACKGROUND

Restricted routes for travelling (e.g., high occupancy vehicle (HOV) lanes, bus lanes, shoulder lanes, etc.) may have different levels of availability and/or access at different times. Traffic may affect travel times of drivers at varying degrees (e.g., traffic may add an hour to a first user's relatively long commute but merely a few minutes to a second driver's relatively shorter commute). In an example, the user may have access to an HOV lane on some days such as when the user is travelling with threshold number of passengers, which may shorten the user's travel time. On other days where the user is not traveling with the threshold number of passengers for the HOV lane, the user may not have access to the HOV lane, which may increase the user's travel time. In an example, the user may see that a bus lane and/or a shoulder lane is empty, but the user may not be permitted to use the bus lane and/or the shoulder lane. Variable travel times may be inconvenient for the user, and may cause the user to miss appointments, dinner reservations, etc. Underutilization of HOV lanes, bus lanes, shoulder lanes, and/or other restricted access road segments may be inefficient for unauthorized drivers that may otherwise take advantage of such travel efficient road segments.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

One or more systems and/or techniques are described herein for providing a user with a route for travelling. In an example of providing a user with a route, a client device, of the user, may be registered to create a registration comprising a license plate of a vehicle of the user. A request for the route, corresponding to a starting location and an ending location, may be received from the client device. A route database may be queried to identify an entry indicating that a restricted access road segment (e.g., a high occupancy vehicle lane, a bus lane, a shoulder lane, etc.) exists between the starting location and the ending location. The route comprising the restricted access road segment may be presented to the user based upon the user being authorized for accessing the restricted access road segment. In an example of authorizing the user, a count of available vehicle allocations may be maintained for the restricted access road segment. Responsive to the count not exceeding an allowed allocation threshold, the user may be authorized for traveling the restricted access road segment. In another example of authorizing the user, the user may be authorized for traveling the restricted access road segment based upon the user submitting a method of payment for access to the restricted access road segment. Responsive to successfully authorizing the user for traveling the restricted access road segment, the route, comprising the restricted access road segment, may be provided to the client device.

In another example of providing a user with a route, a client device, of the user, may be registered to create a registration comprising a license plate of a vehicle of the user. A request for the route, corresponding to a starting location and an ending location, may be received by the client device of the user. A route database may be queried to identify an entry indicating that a traffic light alteration capability exists along a road segment between the starting location and the ending location. Responsive to successfully authorizing the user for traveling the road segment with the traffic light alteration capability, the route may be provided to the client device. A current location of the client device may be maintained. Operation of a traffic light along the road segment may be altered based upon the current location of the client device being within a threshold distance of the traffic light.

In another example of providing a user with a route, a client device, of the user, may be registered with a route planning service. A request for the route, corresponding to a starting location and an ending location, may be sent from the client device. An option to pay for access to the route comprising a restricted access road segment may be received by the client device. Payment may be submitted for the option, and the route may be received by the client device.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
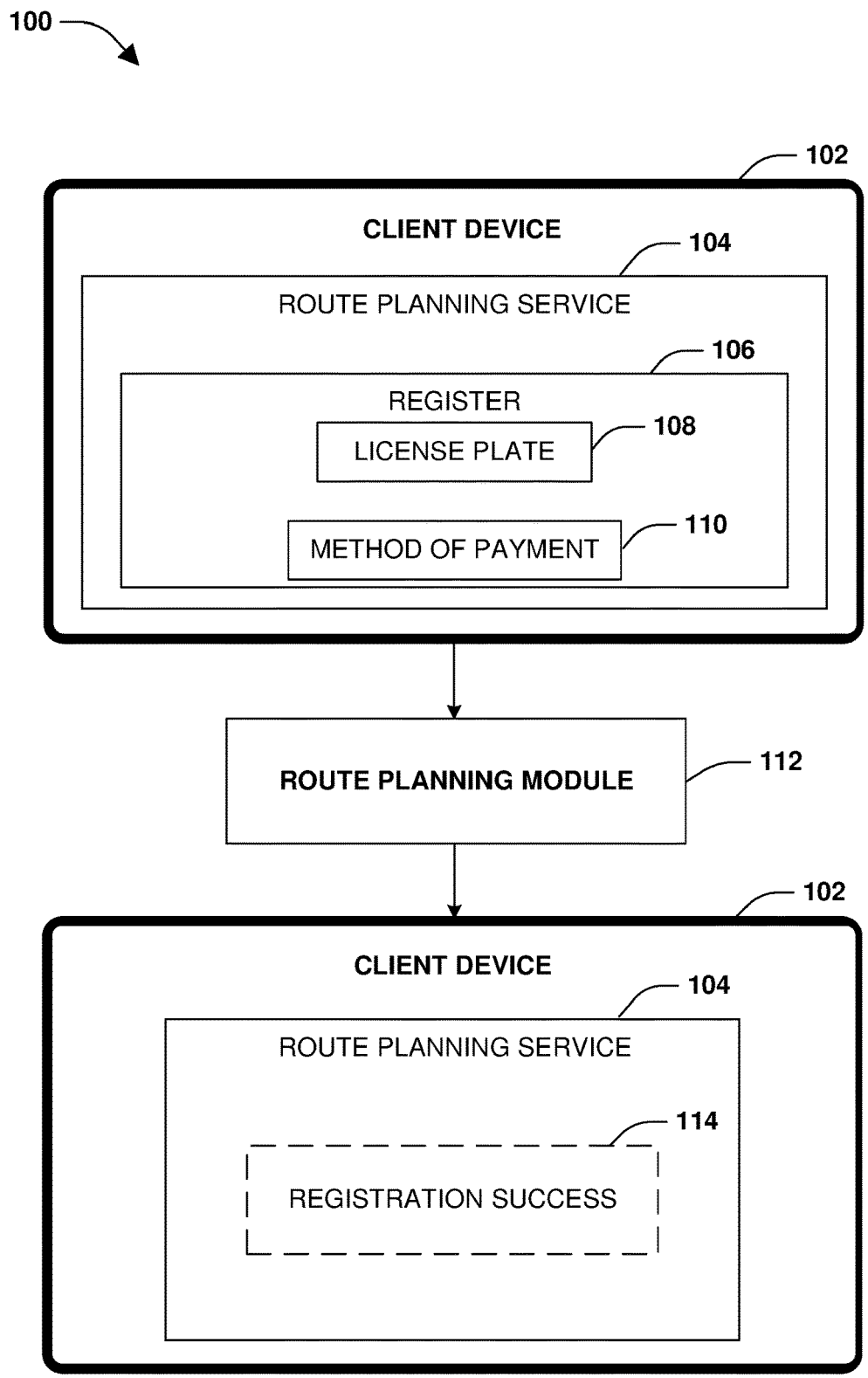
FIG. 1 is an illustration of example system for providing a user with access to a route for travelling, where a client device is registered.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques for providing a route to a user for travelling are provided herein. Traffic may vary based the time and/or day. Users of vehicles may wish to use restricted access road segments (e.g., high occupancy vehicle (HOV) lanes, bus lanes, shoulder lanes, etc.), however, depending on local, state, or other regulations about the restricted access road segments, the user may not have access to the restricted access road segments. In an example, a user, while stuck in traffic, may observe a bus lane that is underutilized. The bus lane may have no traffic, and the user may desire access to the bus lane. However, the user may not have access to the bus lane. In some instances, the user may be late and/or miss appointments, dinner reservations, etc., based upon being stuck in traffic.

Accordingly, as provided herein, users may be provided with access to an efficient route for traveling. In particular, the route may comprise a restricted access road segment (e.g., HOV lanes, bus lanes, shoulder lanes, etc.) and/or a road segment (e.g., the road segment may comprise a traffic light alteration capability). The user, on a client device, may send a request for the route. The request may correspond to a starting location and an ending location. A route planning module may communicate with a state entity (e.g., city government, state government, etc.) to identify the route comprising the restricted access road segment and/or the road segment, and provide the route to the client device based upon various criteria and/or conditions being met (e.g., an availability of allocations for using an HOV lane, payment by the user to utilize a should lane, etc.). The ability to provide users with efficient routes for travelling may reduce travel times of users, expenditure of natural resources (e.g., reduce gas consumption of vehicles otherwise sitting traffic near underutilizes HOV lanes), and/or underutilization of infrastructure such as HOV lanes, bus lanes, etc.

FIG. 1 illustrates an example system 100 for providing users with access to a route for travelling, where a client device 102 is registered. A user of the client device 102 may access a route planning service 104 (e.g., an application, a website, etc.). The route planning service 104 may display an option to register 106 the client device 102. The option to register 106 may comprise a license plate field 108 (e.g., where the user may enter a license plate number of a vehicle of the user) and/or a method of payment field 110 (e.g., where the user may enter a method of payment, such as a credit card number, a debit card number, bank account information, a digital account, etc.). Responsive to the user selecting the option to register 106, the client device 102 may provide registration information (e.g., the license plate number and/or the method of payment) to a route planning module 112. The route planning module 112 may determine whether the license plate number is valid (e.g., by communicating with a motor vehicle monitoring agency, such as a motor vehicle administration (MVA), a department of motor vehicles (DMV), etc.) and/or whether the method of payment is valid. Responsive to the route planning module 112 determining that the method of payment and/or the license plate number is valid, the route planning module 112 may provide a registration notification to the client device 102. The client device 102 may display a registration success 114 notification to the user.

Figure 2:
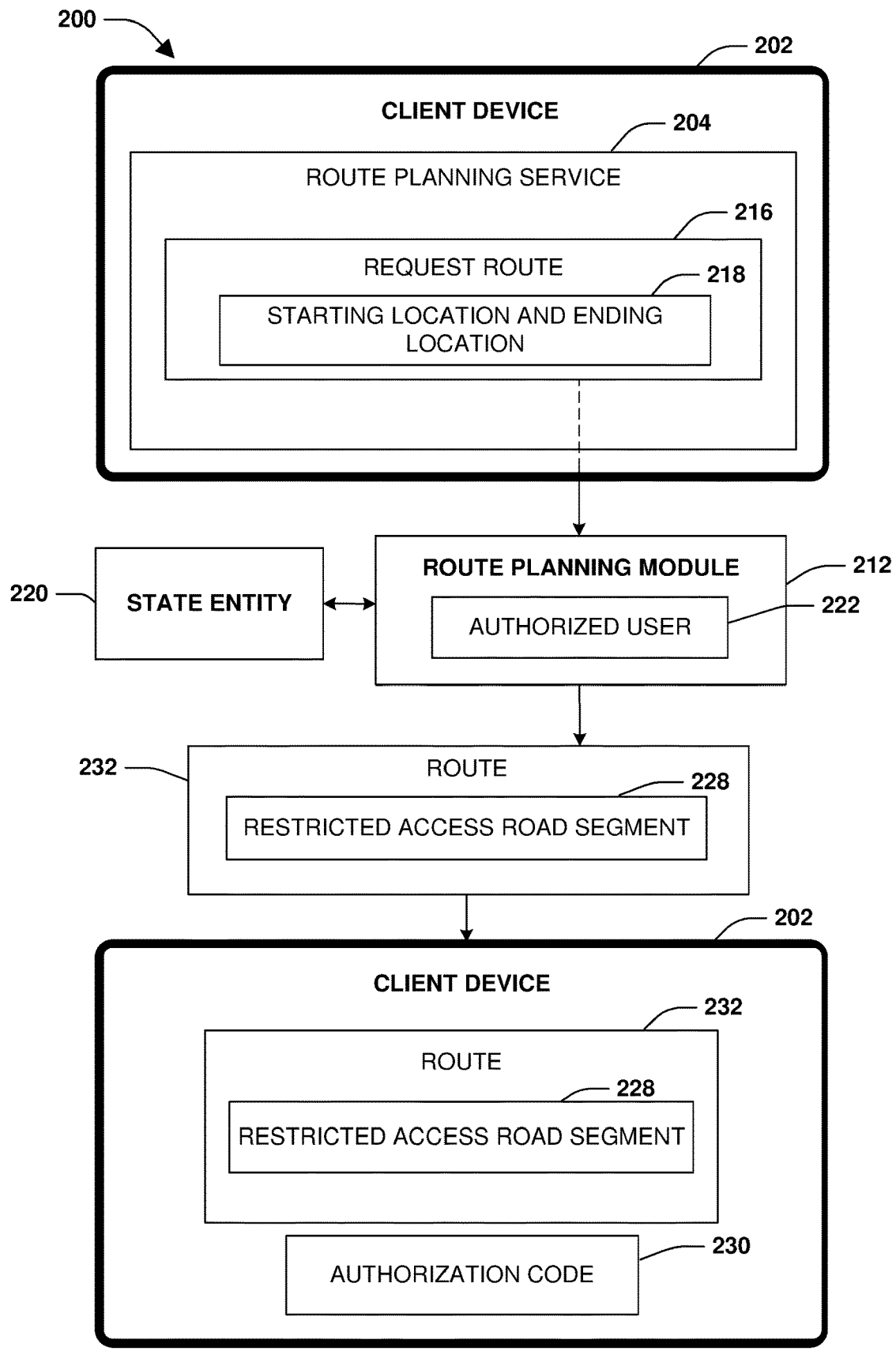
FIG. 2 is an illustration of example system for providing a user with access to a route for travelling, where the user is provided with access to a restricted access road segment.

FIG. 2 illustrates an example system 200 for providing users with access to a route 232 for travelling. The route 232 may comprise a restricted access road segment 228. A user, of a client device 202, may access a route planning service 204 through which the user may request 216 the route 232. The request 216 may correspond to a starting location and an ending location 218. In an example, the starting location may be entered manually by the user or may correspond to a current location of the user (e.g., as determined by a global positioning system (GPS)).

The request 216 may be received by a route planning module 212. The route planning module 212 may be in communication with a state entity 220 (e.g., a DMV, a MVA, a department of transportation, a traffic management system, etc.). In an example, the route planning module 212 module may query a route database (e.g., a database comprising restricted access road segments) to determine whether the route database comprises an entry specifying that the restricted access road segment 228 exists between the starting location and the ending location 218.

Responsive to the restricted access road segment 228 existing between the starting location and the ending location 218, the route planning module 212 may determine whether the user is an authorized user 222 (e.g. determining that the user has a valid method of payment). The user may submit payment to the route planning service 204. The payment may be based upon a time of day and/or a volume of traffic on or around a traditional route (e.g., a route without the restricted access road segment) that the user would typically take. For example, if a super highway in Trafficvillle has a high traffic volume (e.g., bumper to bumper traffic), then the payment may be higher for bumper to bumper traffic conditions than for traffic conditions where traffic is merely moving slowly.

Based upon the user being the authorized user 222, an authorization code 230 (e.g., a code for verification by an officer of the state entity, which may indicate that the user is authorized to access the restricted access road segment 228) may be generated for providing access to the restricted road segment 228. In an example, the route planning module 212 may generate the authorization code 230 and send the authorization code 230 to the state entity 220. In another example, the state entity 220 may generate the authorization code 230 and send the authorization code 230 to the route planning module 212.

In an example, a list of allowed users having access to the restricted access road segment 228 may be maintained by the route planning module 212. Responsive to successfully authorizing the user, vehicle identification information of a vehicle of the user (e.g., a license plate number) may be added to the list of allowed users. The list of allowed users may be provided to the state entity 220. In another example, the state entity 220 may add the user's license plate number (e.g., that the user supplied to the route planning module 212 during registration) to the list of allowed users for the restricted access road segment 228. In an example, if the officer of the state entity observes the user in the restricted access road segment 228, then the officer may check the list of allowed users to determine if the user's license plate is present on the list or the officer may stop the user and ask for the authorization code 230.

The route planning module 212 may send the route 232, comprising the restricted access road segment 228, and/or the authorization code 230 to the client device 202. The client device 202 may display the route 232 and/or the authorization code 230 to the user. Upon arrival at the ending location, the user may be charged based upon an amount of time saved by using the restricted access road segment 228. For example, if the typical drive time from the starting location to the ending location, not using the restricted access road segment 228, is one hour and the user arrives at the ending location in 45 minutes, then the user may be charged based upon the 15 minutes of time that the user saved (e.g., at a rate of a dollar per one minute).

Figure 3A:
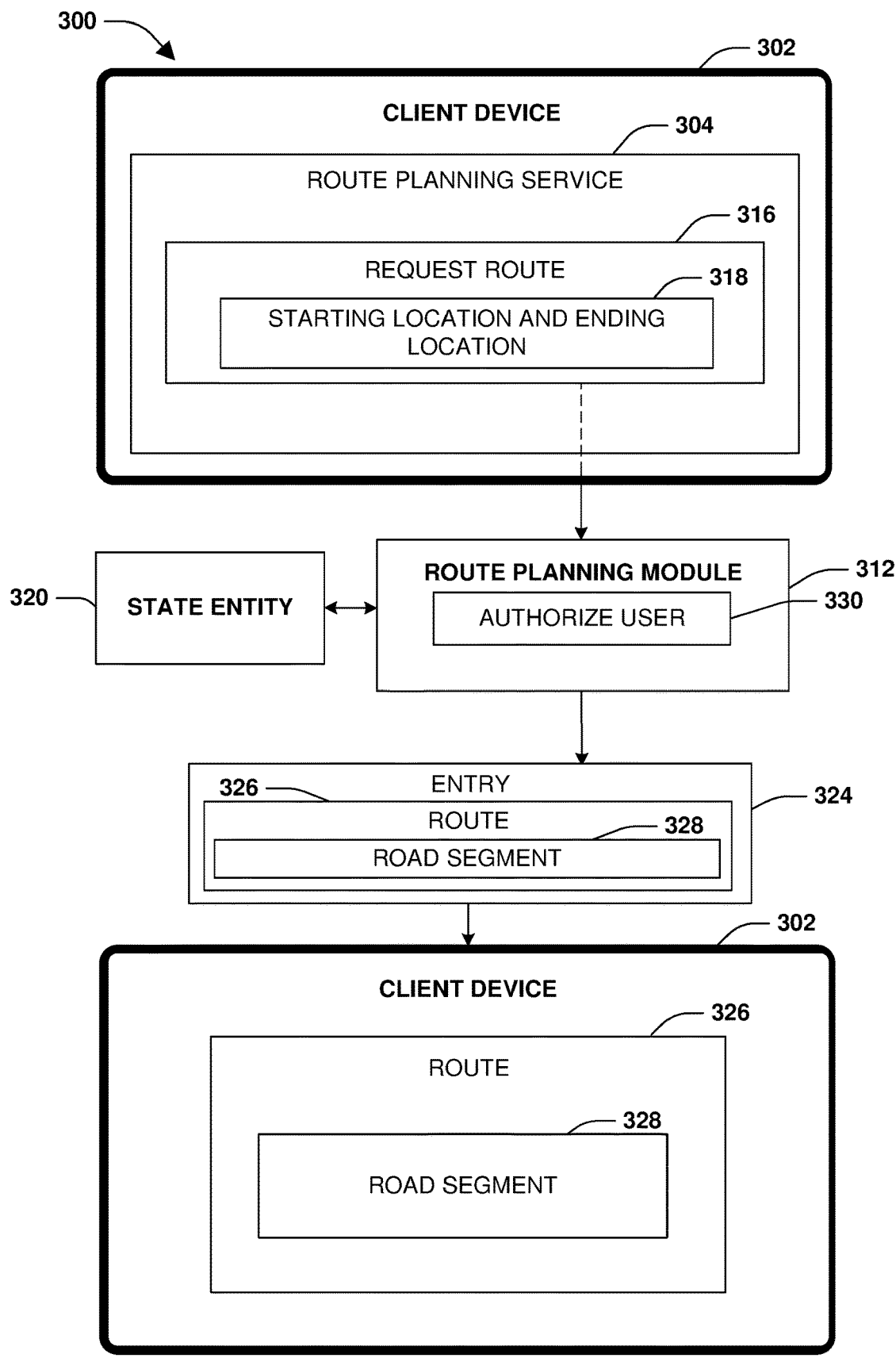
FIG. 3A is an illustration of example system for providing a user with access to a route for travelling, where the user is provided with access to a road segment comprising a traffic light alteration capability.
Figure 3B:
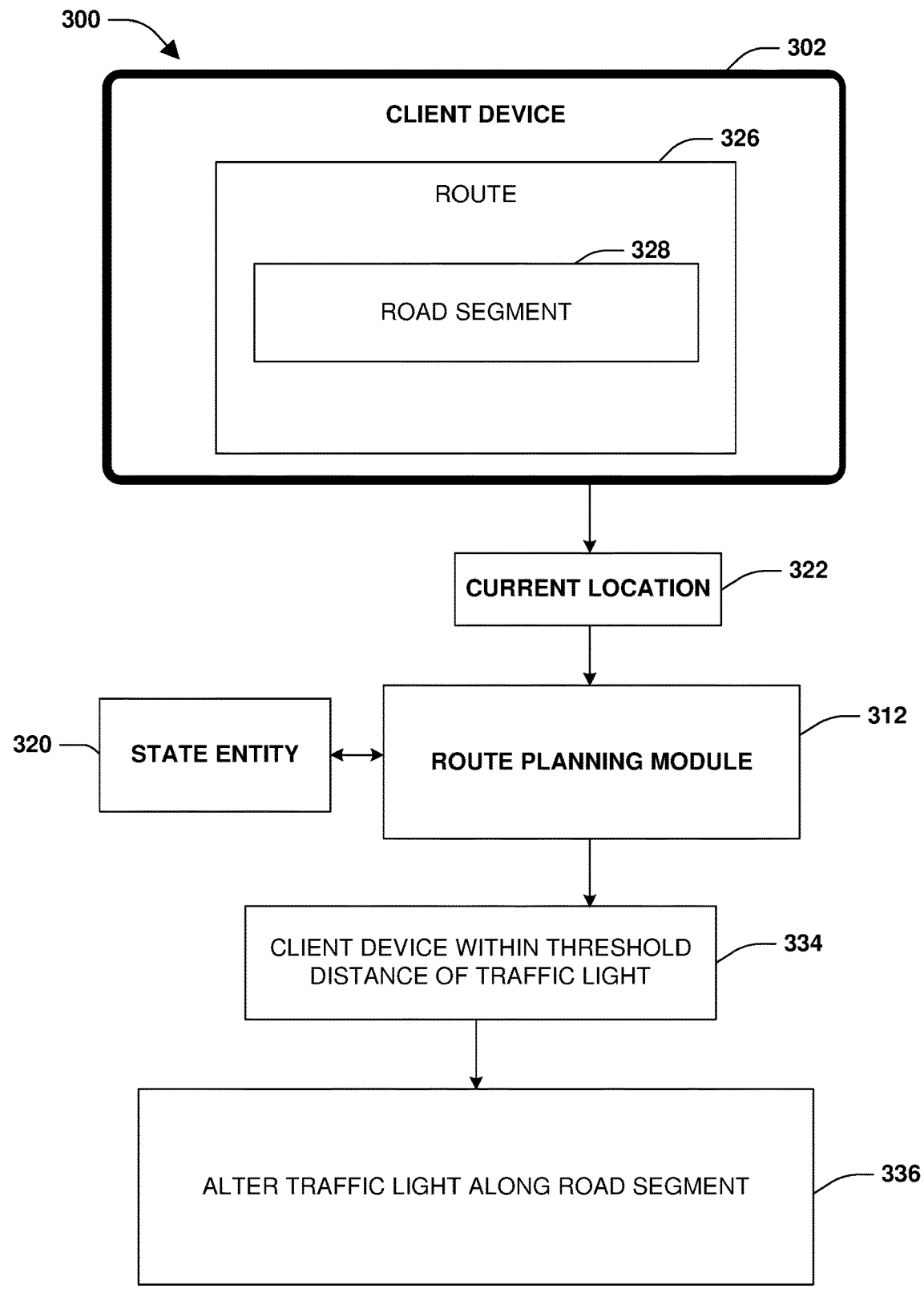
FIG. 3B is an illustration of example system for providing a user with access to a route for travelling, where a current location of the user is used to alter a traffic light along a road segment.

FIGS. 3A-3B illustrate an example system 300 for providing users with access to a route 326 for travelling. The route 326 comprises a road segment 328 having a traffic light alteration capability. A user, of a client device 302, may access a route planning service 304 and request 316 the route 326. The request 316 may correspond to a starting location and an ending location 318. The request 316 may be received by a route planning module 312. The route planning module 312 may be in communication with a state entity 320. In an example, the route planning module 312 may query a route database to determine whether the route database comprises an entry indicating that the road segment 328 exists between the starting location and the ending location 318.

Responsive to the road segment 328 existing between the starting location and the ending location 318, the route planning module 312 may determine that the user is an authorized user 330. The user may submit payment to the route planning service 304, prior to the route planning module 312 providing the route 326 to the user. The route planning module 312 may provide the route 332, comprising the road segment 328, to the client device 302. The client device 302 may display the route 326 to the user.

FIG. 3B illustrates the example system 300 for providing users with access to the route 326, where operation of a traffic light along the road segment 328 of the route 326 is altered. The route planning module 312 may maintain a current location 322 of the client device 302 (e.g., by receiving a GPS location from the client device 302). The route planning module 312 may maintain a traffic light location of the traffic light (e.g., such as provided by the state entity 320). Responsive to the current location 322 of the client device 302 being within a threshold distance 334 of the traffic light location, the route planning module 312 may alter 336 operation of the traffic light along the road segment 328 (e.g., change the traffic light from red to green). The threshold distance 334 may correspond to a speed limit on the road segment 328. For example, if the speed limit is 25 mph, the threshold distance 334 may be less than if the speed limit is 45 mph, because the user may traverse the distance more quickly at higher rates of speed.

Upon arrival at the ending location, the user may be charged based upon an amount of time saved by using the road segment 328 and/or may be charged based upon a number of traffic lights altered. For example, if 3 traffic lights are altered along the road segment 328, then the user may be charged (e.g., at a rate of $2 a traffic light) $6 for the access to the road segment 328.

Figure 4A:
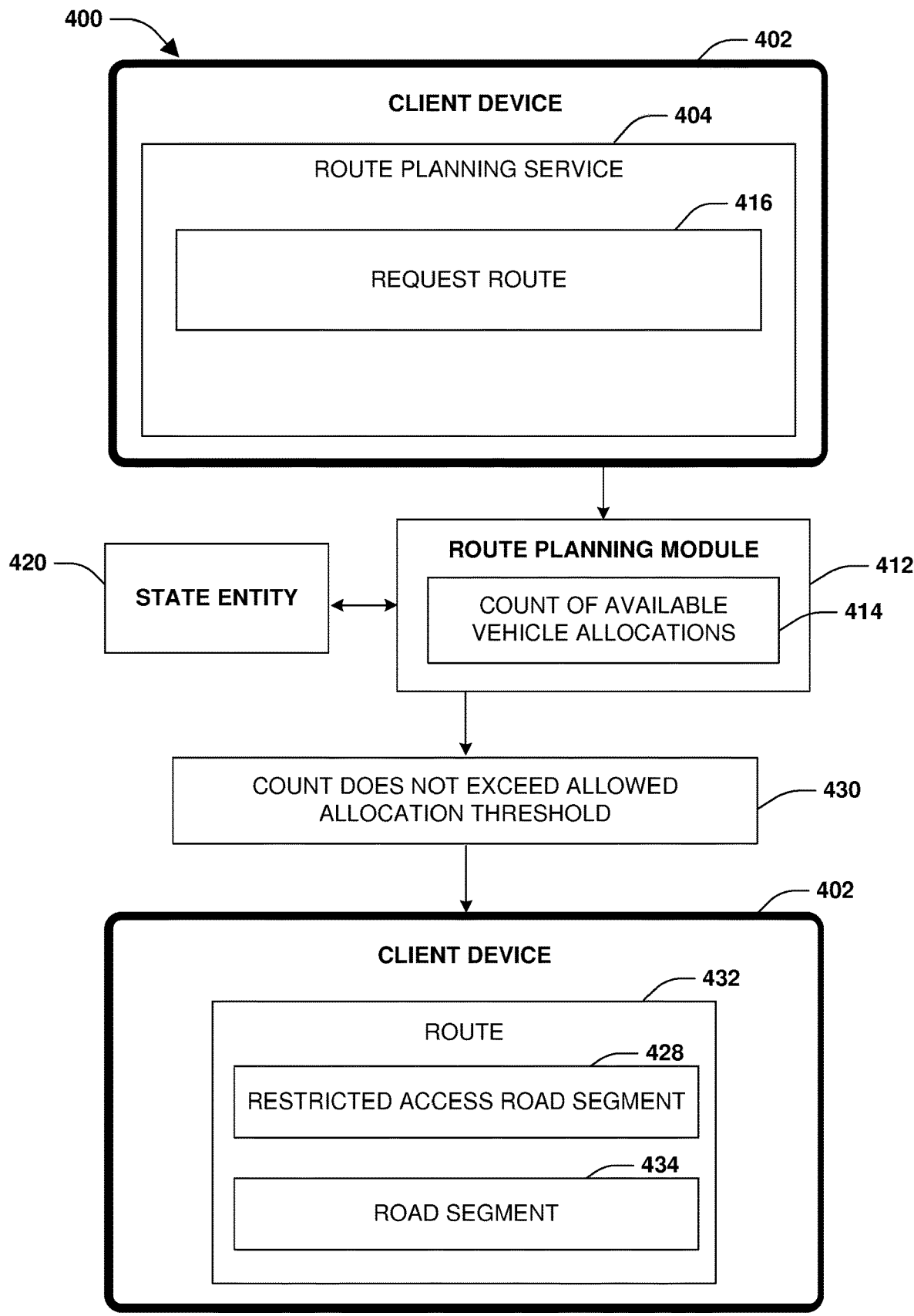
FIG. 4A is an illustration of example system for providing a user with access to a route for travelling, while maintaining a count of available vehicle allocations.
Figure 4B:
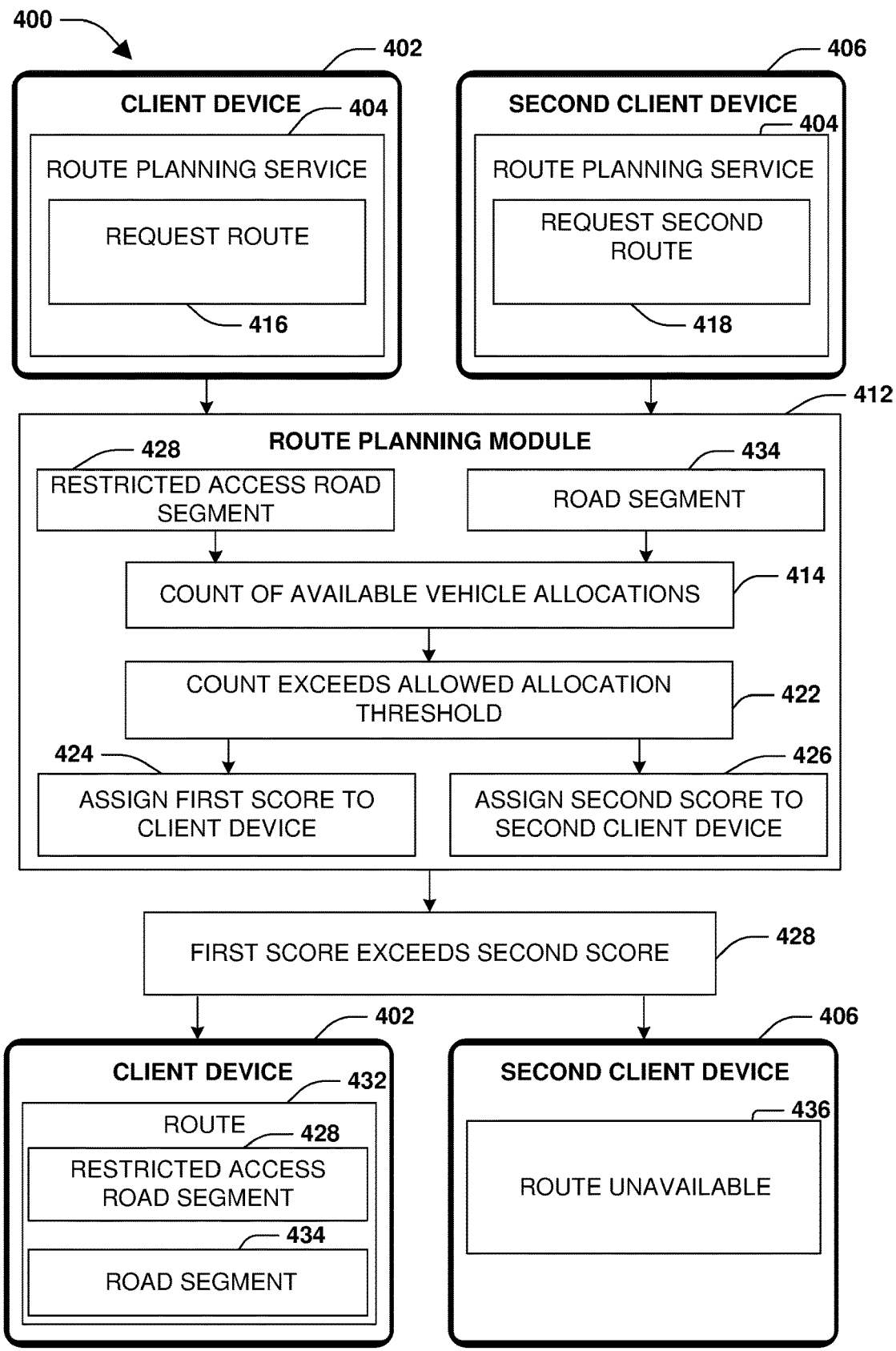
FIG. 4B is an example system for providing a user, but not a second user, with access to a route for travelling based upon the user having a first score exceeding a second score of the second user.

FIGS. 4A-4B illustrate an example system 400 for providing users with access to a route 432, where a count of available vehicle allocations 414 is maintained. FIG. 4A illustrates an example where an allowed allocation threshold is not exceeded 430. Responsive to a user, of a client device 402, requesting 416 the route 432 through a route planning service 404 (e.g., in communication with a state entity 420), a route planning module 412 may identify an entry comprising a restricted access road segment 428 and/or a road segment 434 (e.g., the road segment 434 comprising a traffic light alteration capability) between a starting location and an ending location (e.g., as disclosed in the request 416).

The route planning module 412 may maintain the count of available vehicle allocations 414. In an example, the route planning module 412 may maintain a count of a number of users that are accessing the restricted access road segment 428 and/or the road segment 434 within a timeframe. In an example, the timeframe may comprise a time from when a first user enters the restricted access road segment 428 and/or the road segment 434 to a time when the first user exit the restricted access road segment 428 and/or the road segment 434. The route planning module 412 may determine whether an addition of a vehicle of the user would exceed the allowed allocation threshold (e.g., 20 vehicles may be allowed to us the restricted access road segment 428 within the timeframe) based upon the count of available vehicle allocations 414.

Responsive to the vehicle exceeding the allowed allocation threshold, the route planning module 412 may not provide the route 432, comprising the restricted access road segment 428 and/or the road segment 434, to the client device 402. Responsive to the vehicle not exceeding 430 the allowed allocation threshold, the route planning module 412 may provide the route 432 to the client device 402. In an example, if the count of available vehicle allocations 414 for the restricted access road segment 428 exceeds the allowed allocation threshold and the count of available vehicle allocations 414 for the road segment 434 does not exceed 430 the allowed allocation threshold, then a route that comprises the road segment 434 but not the restricted access road segment 428 may be provided.

FIG. 4B illustrates an example where the allowed allocation threshold 430 is exceeded 422. A second user of a second client device 406 may send a second request 418 for the route 432 (e.g., comprising the same restricted access road segment 428 and/or road segment 434 as what was requested by the user of the client device 402) through the route planning service 404. The second request 418 may be received by the route planning module 412 within a conflicting timeframe as the request 416 (e.g., such that if the user and the second user access the route 432, then both users would be on the route 432 at a similar time). The route planning module 412 may use the count of available vehicle allocations 414 to determine if the request 416 and/or the second request 418 may cause a number of vehicles on the restricted access road segment 428 and/or road segment 434 to exceed 422 the allowed allocation threshold 430.

In an example where the allowance of a single user, but not both users, would not exceed 422 the allowed allocation threshold 430, a first score 424 may be assigned to the client device 402 and a second score 426 may be assigned to the second client device 406. The first score 424 may be based upon the user comprising a preferred user (e.g., a gold level user, a user who pays a slightly higher premium for membership, a user that provides vehicle telemetry to the route planning module, etc.), a handicapped user (e.g., as recognized by a state entity), and/or a frequent user (e.g., a user that uses the route planning service 412 often, such as at least once a week, once a month, etc.). The second score 426 may be assigned based upon the second user comprising a preferred user, a handicapped user, and/or a frequent user. In an example, if the user comprises a handicapped user, a preferred user, and/or a frequent user, and the second user does not comprise a handicapped user, a preferred user, and/or a frequent user, then the first score 424 may exceed 428 the second score 426. Responsive to the first score 424 exceeding 428 the second score 426, the route 432 may be provided to the client device 402 and not the second client device 406. The second client device 406 may receive a notification that the route is available 436.

Figure 5:
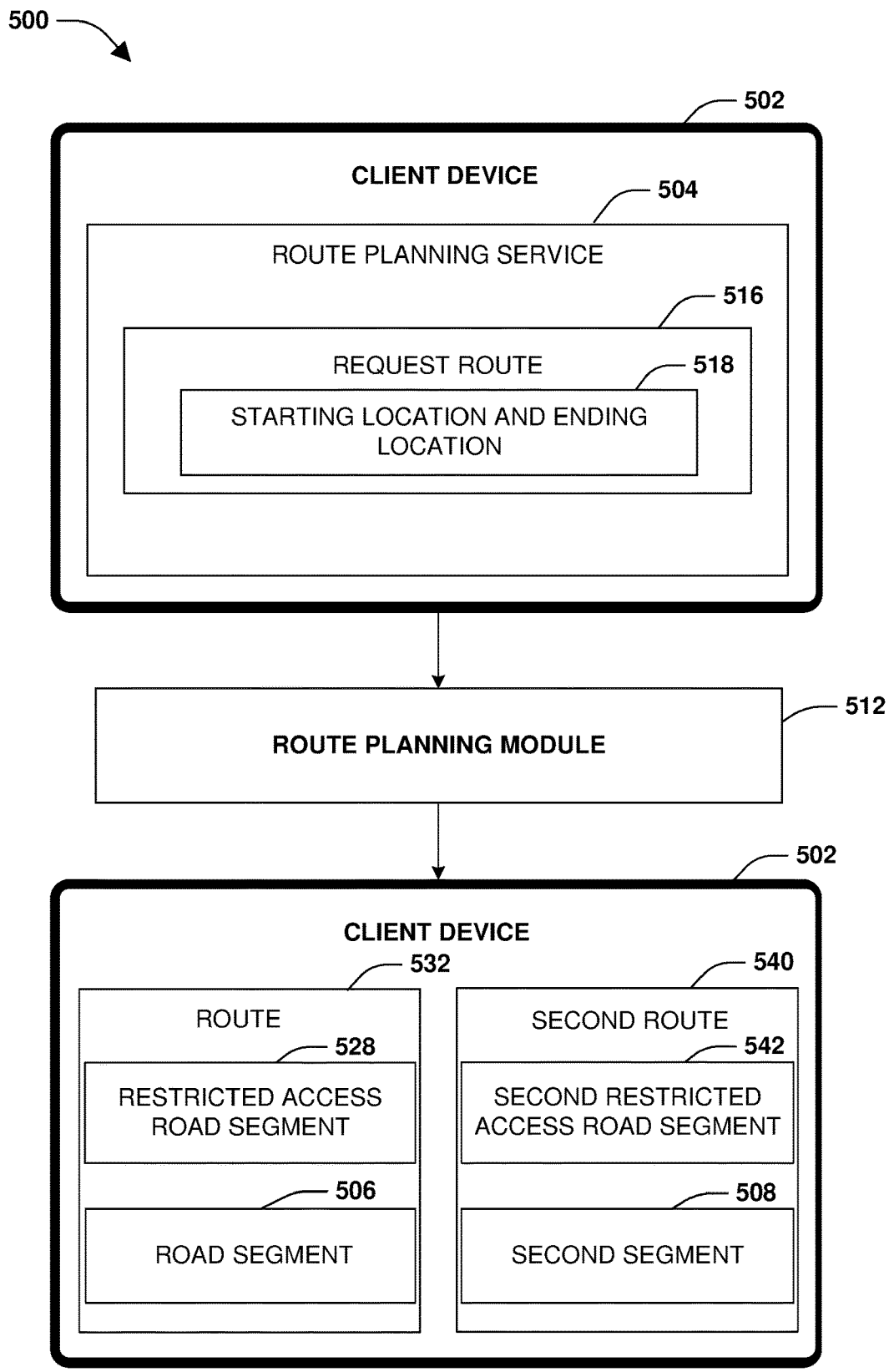
FIG. 5 is an example system for providing a user with an option to access a route and a second route for travelling.

FIG. 5 illustrates an example system 500 for providing users with access to a route 532 and/or a second route 540. A user, of a client device 502, may send a request 516, corresponding to a starting location and an ending location 518, through a route planning service 504 to a route planning module 512. The route planning module 512 may identify an entry comprising the route 532 and a second entry comprising the second route 540. The route 532 may comprise a restricted access road segment 528 and/or a road segment 506 (e.g., comprising a traffic light alteration capability). The second route 540 may comprise a second restricted access road segment 542 and/or a second road segment 508 (e.g., comprising the traffic light alteration capability).

Responsive to the route planning module 512 identifying the entry and the second entry, the route planning module 512 may provide the route 532 and the second route 540 to the client device 502. The user may select the route 532 or the second route 540. An estimated payment amount for the route 532 and the second route 540 may be presented to the user. Responsive to the user selecting the route 532, the client device 502 may display the route 532. Responsive to the user selecting the second route 540, the client device 502 may display the second route 540.

Figure 6:
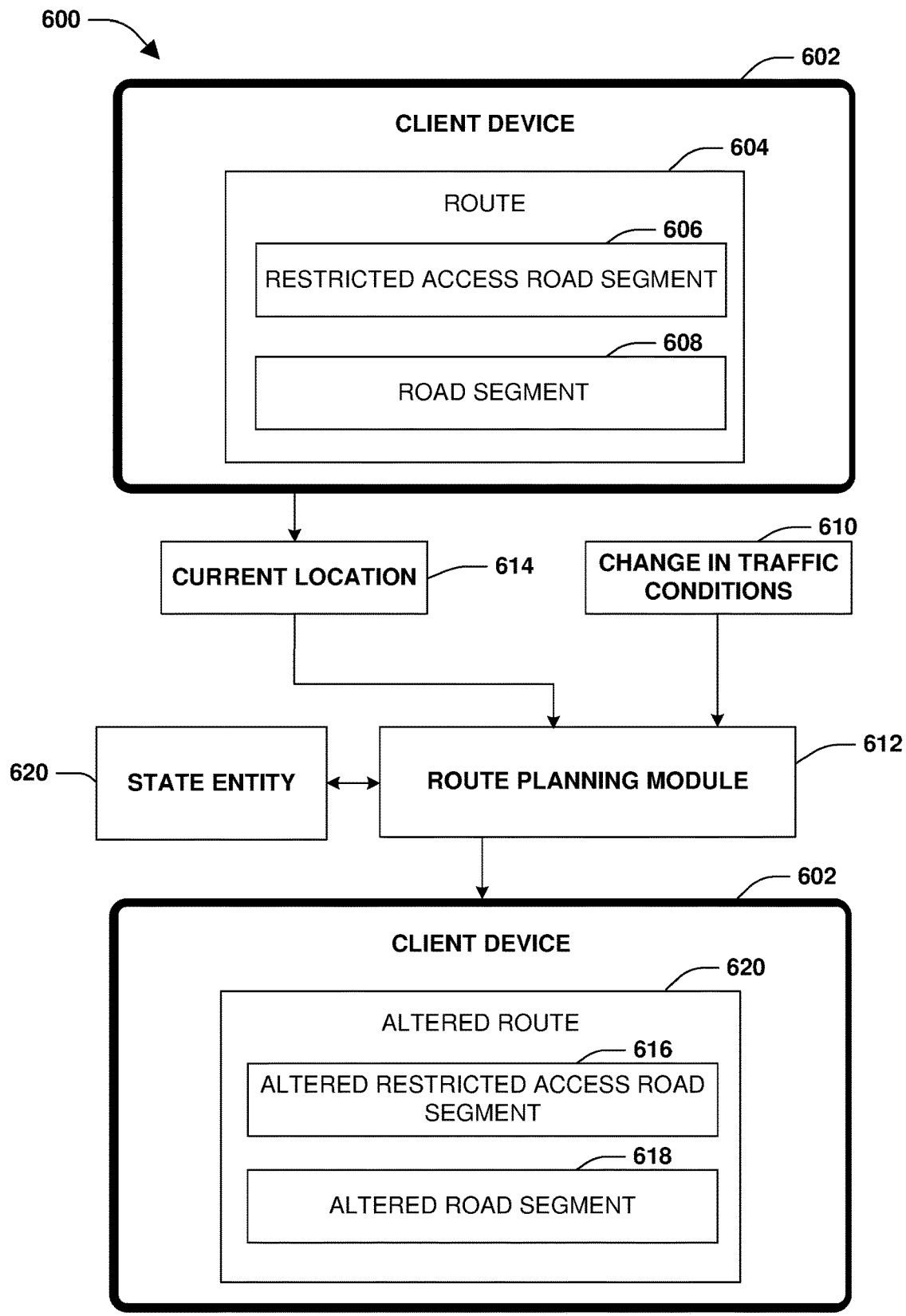
FIG. 6 is an example system for providing a user with access to an altered route for travelling.

FIG. 6 illustrates an example system 600 for providing users with access to an altered route 620 based upon a current location 614 of the user and a change in traffic conditions 610 (e.g., as compared to traffic conditions at a time a route 604 was provided to the user). The user, on a client device 602, may be accessing the route 604 comprising a restricted access road segment 606 and/or a road segment 608. The client device 602 may share the current location 614 of the client device 602 with a route planning module 612. Responsive to the change in traffic conditions 610, the route planning module 612, in communication with a state entity 620, may determine if an entry exists in a route database comprising the altered route 620 between the current location 614 and an ending location. The altered route 620 may comprise an altered restricted access road segment 616 and/or an altered road segment 618. Responsive to determining that the user is authorized to access the altered restricted access road segment 616 and/or the altered road segment 618, the altered route 620 may be provided to the client device 602.

Figure 7:
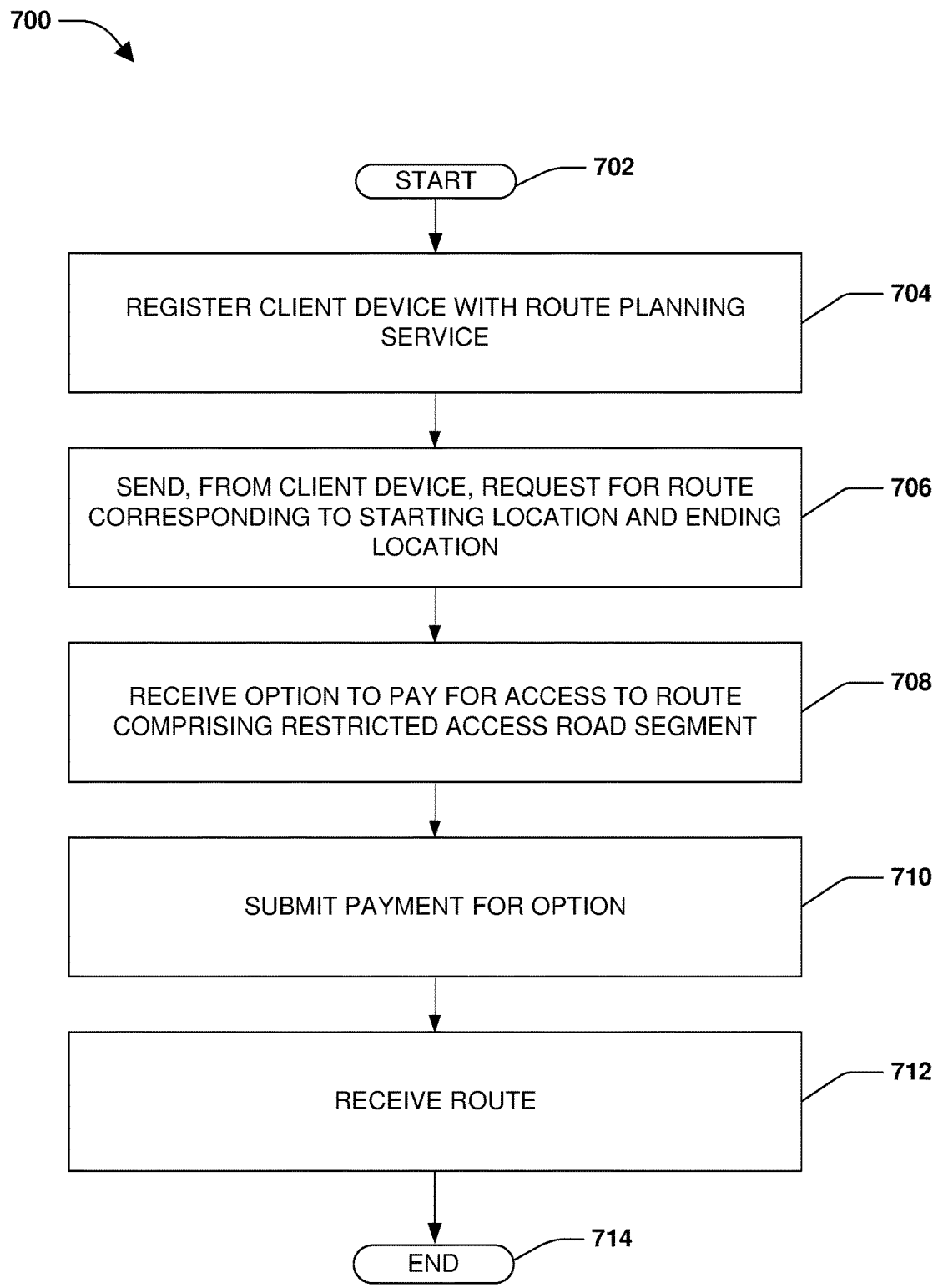
FIG. 7 is an example method for providing a user with access to a route for travelling.

FIG. 7 illustrates a method 700 of providing users with access to a route for travelling. At 702 the method 700 starts. At 704, a user, of a client device, may register the client device with a route planning service. The registration may comprise providing the route planning service with a method of payment and/or a license plate number of a vehicle of the user. At 706, the user may send, from the client device, a request for the route corresponding to a starting location and an ending location. The route planning service may identify the route comprising a restricted access road segment. At 708, the client device may receive an option to pay for access to the route comprising the restricted access road segment. The user may use the method of payment that the user submitted while registering the client device. At 710, the user may submit payment for the option. At 712, the client device may receive the route. At 714, the method 700 ends.

Figure 8:
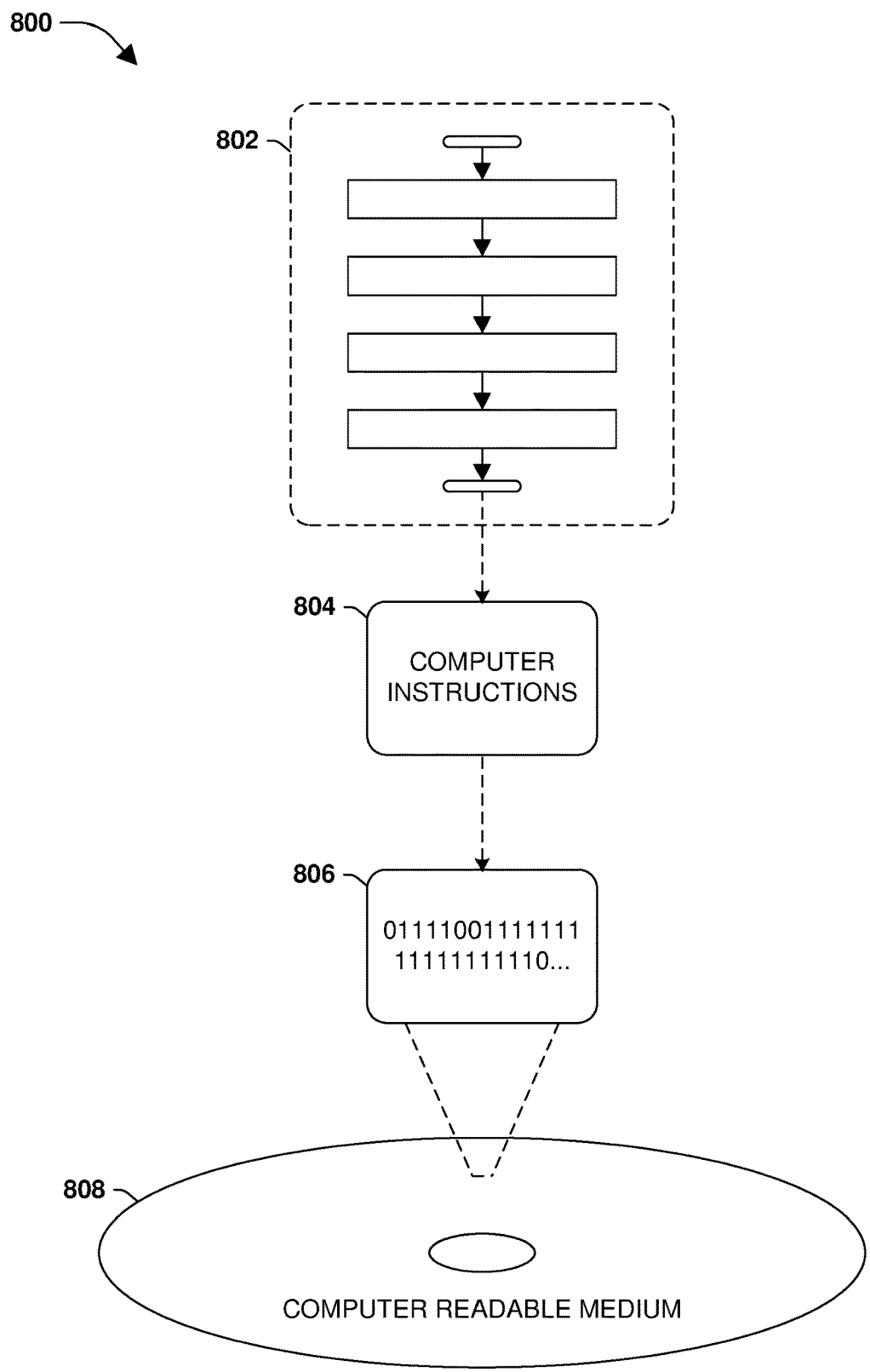
FIG. 8 is an illustration of an example computer-readable medium wherein processor-executable instructions configured to embody one or more of the provisions set forth herein may be comprised.

Still another embodiment involves a computer-readable medium comprising processor-executable instructions configured to implement one or more of the techniques presented herein. An exemplary computer-readable medium that may be devised in these ways is illustrated in FIG. 8, wherein the implementation 800 comprises a computer-readable medium 802 (e.g., a CD-R, DVD-R, or a platter of a hard disk drive), on which is encoded computer-readable data 804. This computer-readable data 804 in turn comprises a set of computer instructions 806 configured to operate according to one or more of the principles set forth herein. In one such embodiment 800, the processor-executable computer instructions 806 may be configured to perform a method 810, such as at least some of the exemplary method 700 of FIG. 7, for example. In another such embodiment, the processor-executable instructions 806 may be configured to implement a system, such as at least some of the exemplary system 100 of FIG. 1, at least some of the exemplary system 200 of FIG. 2, at least some of the exemplary system 300 of FIGS. 3A-3B, at least some of the exemplary system 400 of FIGS. 4A-4B, at least some of the exemplary system 500 of FIG. 5, and/or at least some of the exemplary system 600 of FIG. 6, for example. Many such computer-readable media 802 may be devised by those of ordinary skill in the art that are configured to operate in accordance with the techniques presented herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

FIG. 8 and the following discussion provide a brief, general description of a suitable computing environment to implement embodiments of one or more of the provisions set forth herein. The operating environment of FIG. 8 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

Figure 9:
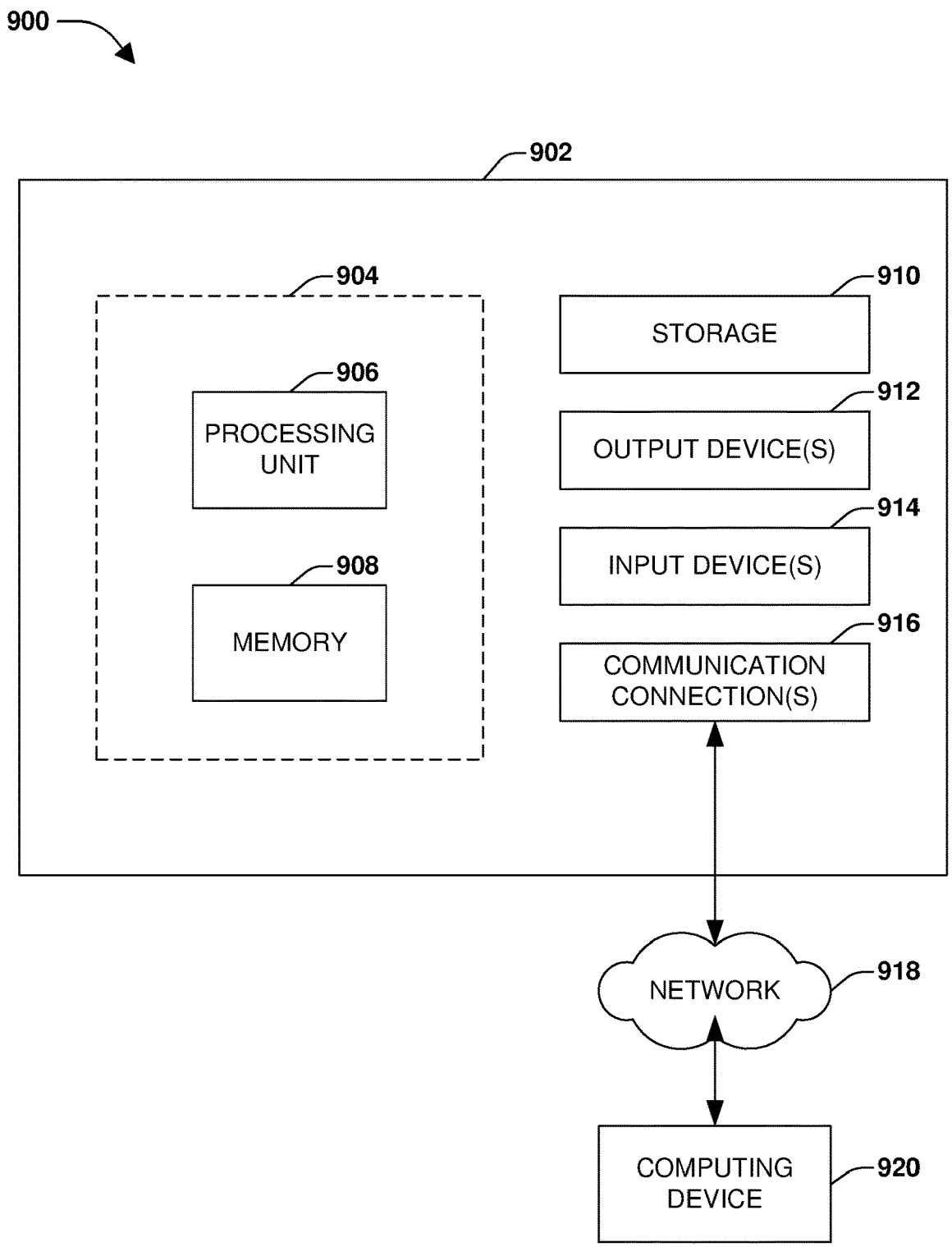
FIG. 9 illustrates an example computing environment wherein one or more of the provisions set forth herein may be implemented.

FIG. 9 illustrates an example of a system 900 comprising a computing device 902 configured to implement one or more embodiments provided herein. In one configuration, computing device 902 includes at least one processing unit 906 and memory 908. Depending on the exact configuration and type of computing device, memory 908 may be volatile (such as RAM, for example), non-volatile (such as ROM, flash memory, etc., for example), or some combination of the two. This configuration is illustrated in FIG. 9 by dashed line 904.

In other embodiments, device 902 may include additional features and/or functionality. For example, device 902 may also include additional storage (e.g., removable and/or non-removable) including, but not limited to, magnetic storage, optical storage, and the like. Such additional storage is illustrated in FIG. 9 by storage 910. In one embodiment, computer readable instructions to implement one or more embodiments provided herein may be in storage 910. Storage 910 may also store other computer readable instructions to implement an operating system, an application program, and the like. Computer readable instructions may be loaded in memory 908 for execution by processing unit 906, for example.

The term "computer readable media" as used herein includes computer storage media. Computer storage media includes volatile and nonvolatile, removable and non-removable media implemented in any method or technology for storage of information such as computer readable instructions or other data. Memory 908 and storage 910 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 902. Any such computer storage media may be part of device 902.

Device 902 may also include communication connection(s) 916 that allows device 902 to communicate with other devices. Communication connection(s) 916 may include, but is not limited to, a modem, a Network Interface Card (NIC), an integrated network interface, a radio frequency transmitter/receiver, an infrared port, a USB connection, or other interfaces for connecting computing device 902 to other computing devices. Communication connection(s) 916 may include a wired connection or a wireless connection. Communication connection(s) 916 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 902 may include input device(s) 914 such as keyboard, mouse, pen, voice input device, touch input device, infrared cameras, video input devices, and/or any other input device. Output device(s) 912 such as one or more displays, speakers, printers, and/or any other output device may also be included in device 902. Input device(s) 914 and output device(s) 912 may be connected to device 902 via a wired connection, wireless connection, or any combination thereof. In one embodiment, an input device or an output device from another computing device may be used as input device(s) 914 or output device(s) 912 for computing device 902.

Components of computing device 902 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 902 may be interconnected by a network. For example, memory 908 may be comprised of multiple physical memory units located in different physical locations interconnected by a network.

Those skilled in the art will realize that storage devices utilized to store computer readable instructions may be distributed across a network. For example, a computing device 920 accessible via a network 918 may store computer readable instructions to implement one or more embodiments provided herein. Computing device 902 may access computing device 920 and download a part or all of the computer readable instructions for execution. Alternatively, computing device 902 may download pieces of the computer readable instructions, as needed, or some instructions may be executed at computing device 902 and some at computing device 920.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "exemplary" is used herein to mean serving as an example, instance, or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean one or more unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based at least in part upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A system of providing users with access to a route for traveling, the system comprising:
   a processor; and
   memory comprising instructions that when executed by the processor cause the processor to:
   receive, from a first client device of a first user, a request for a route corresponding to a starting location and an ending location;
   query a route database to identify an entry indicating that a restricted access road segment with a traffic light alteration capability exists between the starting location and the ending location;
   receive, from a second client device of a second user, a second request for a second route corresponding to the restricted access road segment;
   based upon a determination that allowance of one of the first user or the second user, but not both the first user and the second user, to use the restricted access road segment would not exceed an allowed allocation threshold:
      assign a first score to the first user; and
      assign a second score to the second user;
   authorize the first user to use the restricted access road segment with the traffic light alteration capability based upon the first user submitting a method of payment for access to the traffic light alteration capability; and
   responsive to successfully authorizing the first user to use the restricted access road segment with the traffic light alteration capability and determining that the first score exceeds the second score:
      provide the route, comprising the restricted access road segment with the traffic light alteration capability, to the first client device but not the second client device;
      maintain a current location of the first client device; and
      alter operation of a traffic light along the restricted access road segment based upon the current location of the first client device being within a threshold distance of the traffic light, wherein the threshold distance corresponds to a speed limit.

2. The system of claim 1, the instructions, when executed by the processor, causing the processor to:
   authorize the first user with a state entity for traveling the restricted access road segment with the traffic light alteration capability.

3. The system of claim 1, wherein the restricted access road segment comprises at least one of a bus lane or a shoulder lane.

4. The system of claim 1, the instructions, when executed by the processor, causing the processor to:
   determine an amount for a payment for access to the restricted access road segment based upon at least one of an amount of time saved by using the restricted access road segment, a time of day, a number of traffic light alterations, or a volume of traffic.

5. The system of claim 1, wherein the first score is assigned based upon the first user comprising at least one of a preferred user, a handicapped user, or a frequent user.

6. The system of claim 1, the instructions, when executed by the processor, causing the processor to:
   responsive to a change in traffic conditions on the route, provide an altered route to the first user based upon the traffic conditions and the current location of the first user.

7. The system of claim 1, the instructions, when executed by the processor, causing the processor to:
   query the route database to identify a second entry indicating that a second road segment with the traffic light alteration capability exists between the starting location and the ending location; and
   offer the route comprising the restricted access road segment and a third route comprising the second road segment to the first user for selection.

8. A method, comprising:
   receiving, from a first client device of a first user, a request for a route corresponding to a starting location and an ending location;
   querying a route database to identify an entry indicating that a restricted access road segment with a traffic light alteration capability exists between the starting location and the ending location;
   receiving, from a second client device of a second user, a second request for a second route corresponding to the restricted access road segment;
   based upon a determination that allowance of one of the first user or the second user, but not both the first user and the second user, to use the restricted access road segment would not exceed an allowed allocation threshold:

assigning a first score to the first user; and
assigning a second score to the second user;
determining an amount for a payment for access to the restricted access road segment based upon a number of traffic light alterations;
authorizing the first user to use the restricted access road segment with the traffic light alteration capability based upon the first user submitting a method of payment for access to the traffic light alteration capability; and
responsive to successfully authorizing the first user to use the restricted access road segment with the traffic light alteration capability and determining that the first score exceeds the second score:
providing the route, comprising the restricted access road segment with the traffic light alteration capability, to the first client device but not the second client device;
maintaining a current location of the first client device; and
altering operation of a traffic light along the restricted access road segment based upon the current location of the first client device being within a threshold distance of the traffic light.

9. The method of claim 8, comprising:
authorizing the first user with a state entity for traveling the restricted access road segment with the traffic light alteration capability.

10. The method of claim 8, wherein the restricted access road segment comprises at least one of a bus lane or a shoulder lane.

11. The method of claim 8, comprising:
charging the first user, for the payment for access to the restricted access road segment, based upon the amount.

12. The method of claim 8, wherein the first score is assigned based upon the first user comprising at least one of a preferred user, a handicapped user, or a frequent user.

13. The method of claim 8, comprising:
responsive to a change in traffic conditions on the route, providing an altered route to the first user based upon the traffic conditions and the current location of the first user.

14. The method of claim 8, comprising:
querying the route database to identify a second entry indicating that a second road segment with the traffic light alteration capability exists between the starting location and the ending location; and
offering the route comprising the restricted access road segment and a third route comprising the second road segment to the first user for selection.

15. A non-transitory computer-readable medium comprising instructions that when executed by a processor perform operations, the operations comprising:
receiving, from a first client device of a first user, a request for a route corresponding to a starting location and an ending location;
querying a route database to identify an entry indicating that a restricted access road segment with a traffic light alteration capability exists between the starting location and the ending location;
receiving, from a second client device of a second user, a second request for a second route corresponding to the restricted access road segment;
based upon a determination that allowance of one of the first user or the second user, but not both the first user and the second user, to use the restricted access road segment would not exceed an allowed allocation threshold:
assigning a first score to the first user; and
assigning a second score to the second user;
authorizing the first user to use the restricted access road segment with the traffic light alteration capability based upon the first user submitting a method of payment for access to the traffic light alteration capability; and
responsive to successfully authorizing the first user to use the restricted access road segment with the traffic light alteration capability and determining that the first score exceeds the second score:
providing the route, comprising the restricted access road segment with the traffic light alteration capability, to the first client device but not the second client device;
maintaining a current location of the first client device; and
altering operation of a traffic light along the restricted access road segment based upon the current location of the first client device being within a threshold distance of the traffic light,
at least one of:
the operations comprising determining an amount for a payment for access to the restricted access road segment based upon a number of traffic light alterations; or
the threshold distance corresponding to a speed limit.

16. The non-transitory computer-readable medium of claim 15, the operations comprising:
authorizing the first user with a state entity for traveling the restricted access road segment with the traffic light alteration capability.

17. The non-transitory computer-readable medium of claim 15, the operations comprising:
charging the first user, for the payment for access to the restricted access road segment, based upon the amount.

18. The non-transitory computer-readable medium of claim 15, wherein the first score is assigned based upon the first user comprising at least one of a preferred user, a handicapped user, or a frequent user.

19. The non-transitory computer-readable medium of claim 15, the operations comprising:
responsive to a change in traffic conditions on the route, providing an altered route to the first user based upon the traffic conditions and the current location of the first user.

20. The non-transitory computer-readable medium of claim 15, the operations comprising:
querying the route database to identify a second entry indicating that a second road segment with the traffic light alteration capability exists between the starting location and the ending location; and
offering the route comprising the restricted access road segment and a third route comprising the second road segment to the first user for selection.

* * * * *